(12) United States Patent
Some et al.

(10) Patent No.: US 8,964,177 B2
(45) Date of Patent: Feb. 24, 2015

(54) METHOD AND APPARATUS TO ILLUMINATE SAMPLE AND CONTAINING VESSEL IN A LIGHT SCATTERING DETECTOR

(71) Applicant: Wyatt Technology Corporation, Santa Barbara, CA (US)

(72) Inventors: Daniel I. Some, Santa Barbara, CA (US); Michael I. Larkin, Santa Barbara, CA (US); Peter G. Neilson, Santa Barbara, CA (US); David N. Villalpando, Lompoc, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 123 days.

(21) Appl. No.: 13/871,429

(22) Filed: Apr. 26, 2013

(65) Prior Publication Data

US 2013/0286381 A1    Oct. 31, 2013

Related U.S. Application Data

(60) Provisional application No. 61/639,717, filed on Apr. 27, 2012.

(51) Int. Cl.
*G01N 15/02* (2006.01)
*G01N 21/51* (2006.01)

(52) U.S. Cl.
CPC ..................... *G01N 21/51* (2013.01)

USPC ........................................... 356/336; 356/338

(58) Field of Classification Search
USPC ......................................................... 356/336
See application file for complete search history.

(56) References Cited

U.S. PATENT DOCUMENTS

| | | | |
|---|---|---|---|
| 5,169,601 A * | 12/1992 | Ohta et al. | 422/73 |
| 6,124,937 A * | 9/2000 | Mittenzwey et al. | 356/432 |
| 6,519,032 B1 | 2/2003 | Kuebler et al. | |
| 6,819,420 B2 | 11/2004 | Kuebler et al. | |
| 2011/0210002 A1 | 9/2011 | Hsieh et al. | |

* cited by examiner

*Primary Examiner* — Roy M Punnoose
(74) *Attorney, Agent, or Firm* — David N. Villalpando; Philip J. Wyatt

(57) ABSTRACT

A method and apparatus for the illumination of a sample are disclosed. An imaging illumination light source is directed to pass through an absorbing/transmitting structure in order to illuminate the sample and any containing vessel. A diffuser may aid in properly dispersing the light from the imaging illumination source. A light sensitive detector such as a camera records an image therefrom. The beam from a light scattering source is directed through the sample and any containing vessel, and upon exiting the sample/vessel, impinges upon the absorbing/transmitting structure selected to absorb at the wavelength of the light scattering source. Scattered light from the sample is collected by a photo detector. Methods of use for the novel lighting system are also disclosed.

32 Claims, 5 Drawing Sheets

METHOD AND APPARATUS TO ILLUMINATE SAMPLE AND CONTAINING VESSEL IN A LIGHT SCATTERING DETECTOR

BACKGROUND

Light scattering is a non-invasive technique for characterizing macromolecules and a wide range of particles in solution. The two types of light scattering detection frequently used for the characterization of macromolecules are static light scattering (SLS) and dynamic light scattering (DLS).

Static light scattering experiments involve the measurement of the absolute intensity of the light scattered from a sample. This measurement allows the determination of the size of the sample molecules, and, when coupled with knowledge of the sample concentration, allows for the determination their weight average molar mass. In addition, nonlinearity of the intensity of scattered light as a function of sample concentration may be used to measure inter-particle interactions and associations.

Dynamic light scattering is also known as quasi-elastic light scattering (QELS) and photon correlation spectroscopy (PCS). In a DLS experiment, time-dependent fluctuations in the scattered light signal are measured using a fast photodetector. DLS measurements determine the diffusion coefficient of the molecules or particles, which can in turn be used to calculate their hydrodynamic radius.

Extensive literature has been published describing methods for making both static and dynamic light scattering measurements in flowing and batch (non-flowing) systems. See, for example, P. J. Wyatt, "Light scattering and the absolute characterization of macromolecules," *Analytica chimica Acta,* 272, 1-40, (1993). Many commercially available instruments allow for the measurement of SLS and/or DLS, and there are many methods to perform these measurements. For example, U.S. Pat. No. 6,819,420, herein incorporated by reference, by Kuebler and Bennet, discloses a method and apparatus for measuring the light scattering properties of a solution in a vessel wherein light may be transmitted into the solution through the bottom of the optically transparent vessel, and the scattered light may be detected through the same surface by means of an optical fiber coupled with a photodiode.

With the development and improvement in the optical quality of multiwell plates, it has become possible to make both SLS and DLS measurements directly from samples contained therein, as described in the above referenced patent by Kuebler, et. al. Methods capable of measuring samples directly in these multiwell plates are generally desirable given both the high-throughput nature of the measurements and the reduced sample volume requirements. Multiwell plates may contain any number of independent wells. For example, some standard plates have 96, 384, 1536 wells or more, each well is able to contain a different sample, and all wells may be tested in a single data collection run. In addition, use of these plates obviates the laborious need to clean and dry individual scintillation vials after each measurement. These plates generally have very low volume wells, and commercially available multiwell plate based measurement instruments are capable of light scattering measurements from sample volumes of 1 µL or less. These tiny sample volumes are of great benefit when one has a limited amount of sample from which to make measurements, particularly when compared to the 300 µL or larger sized measurement volumes often required by other light scattering techniques.

All light scattering measurements are subject to various sources of unwanted noise, which can lead to inaccurate measurements of the light scattering properties of the sample. This noise may be due to unknown contaminants present in the sample, soiled or improperly manufactured or maintained or dirty surfaces of the vessel through which the light transmitted and/or measured passes. Imperfections in the surfaces of the vessel or other contaminants contained therein or adhered thereto, such as bubbles, precipitated particles, residue, etc., may also cause background scattering which can also interfere with proper measurements of scattered light from the sample or may interfere with the beam or scattered light expected to exit the vessel and be measured by a detector. In other words, deleterious high background signal, or noise, is caused by light scattered from anything other than the sample. This background noise decreases the light scattering instrument's sensitivity due to the increase in the noise present in relation to the useful signal scattered from the sample itself, and therefore an overall reduction in the signal-to-noise ratio upon which the sensitivity of the measurement is dependent. For DLS measurements, higher sample concentrations of precious sample materials are required to overcome this background signal. It is therefore important to be aware of any possible sources for high background signal, and it is an objective of this invention to provide means for detection of such sources.

Light scattering detection in multiwell plates has many advantages, including high throughput, the ability to control the temperature of multiple samples simultaneously, the ability to monitor aggregation and other self and hetero associations, etc. However, there are special pitfalls associated with such measurements. For example, gas bubbles may adhere to the bottom or side of the well, or may float within the sample itself or at or near the fluid meniscus. In addition, multiwell plates may be reused, and thus careful cleaning is required between sample collections; imperfect washing may leave behind artifacts or residues which can deleteriously affect light scattering measurements. The amount of time required of an operator or a robotic injector to fill an entire plate opens up the possibility for dust particles to fall into the wells or other contaminants to be introduced thereto by the handling of the plates while loading wells, such as oil from skin, powder from handling gloves, cosmetics, flaking skin cells, debris from loading pipettes. In order to mitigate problems associated with evaporation, an oil overlay is often used to "cap" a well, and residues and/or droplets from this oil may remain in a well. Alternatively, a layer of film may also be applied to the top surface of the plate to mitigate evaporation, and debris from these films may also contaminate wells, ultimately causing inaccurate measurements of the light scattering properties of the samples contained therein.

It is therefore of critical importance that light scattering measurements be made under as pristine conditions as possible. It is further critical that any analysis done on light scattering data be performed with knowledge of the condition of the vessel in which the measurement is made, and that any issues which might affect the background scattering be known at or before the time of analysis. It is an objective of this invention to supply information on potentially contaminated wells prior to analysis of data collected from samples therein.

BRIEF DESCRIPTION OF THE INVENTION

In order to better understand the status and reliability of data collected from a light scattering measurement of a liquid sample, new means of illumination of the sample, and when appropriate, the containing vessel and methods of using these means are disclosed. In one embodiment of the invention, an imaging illumination light source is directed to an absorbing/transmitting optical structure which absorbs light at and near a selected wavelength located proximate to the sample and any containing vessel. A light scattering source operating at a wavelength that is selected to be absorbed by the absorbing/transmitting optical structure is directed through sample, and is subsequently at least partly absorbed by the absorbing/transmitting optical structure. Light scattered from the sample by the light scattering source is detected and measured by a measuring means such as a photodiode, avalanche photodiode (APD), photomultiplier tube (PMT), etc., which may have been directed thereto by an optical fiber. The beam created from the image illumination light source is transmitted through or reflected by the plate, and optionally, a diffuser, which illuminates the sample and any containing vessel. One or more cameras may then be utilized to record optical images of the illuminated sample and any containing vessel. Many other embodiments and methods for use thereof are also disclosed.

DETAILED DESCRIPTION OF THE INVENTION

Figure 1:
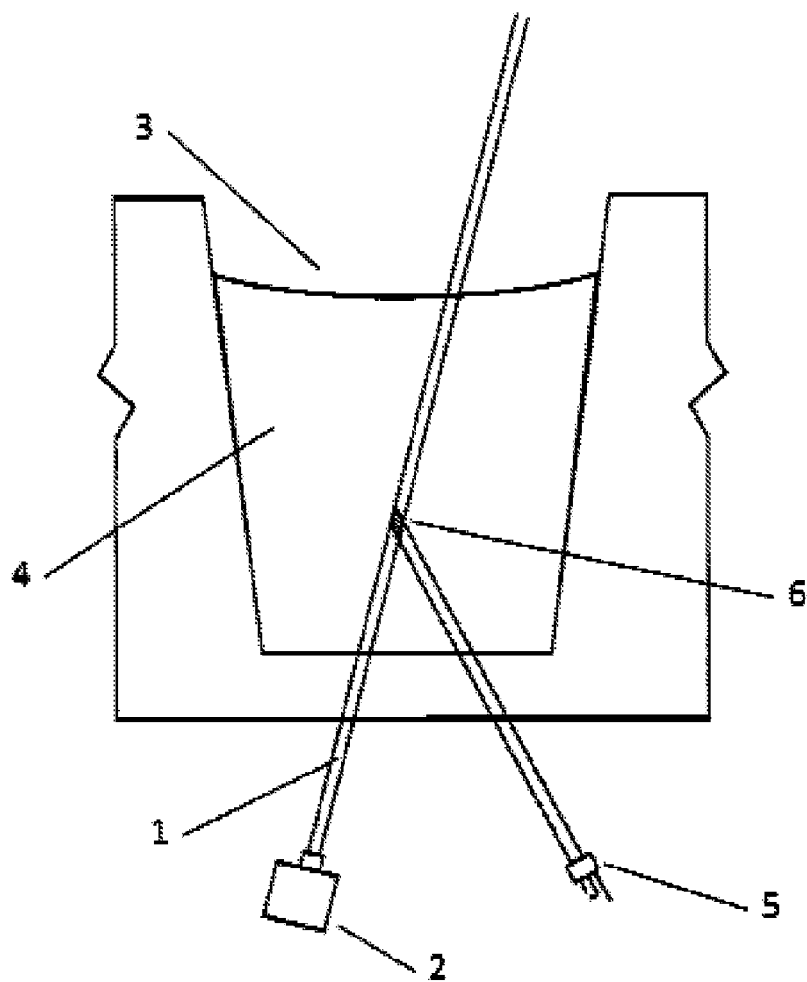
FIG. 1 illustrates a conventional dynamic light scattering measurement system for a single well of a multiwell plate.

Light scattering detection is an important means by which information about particles and molecules in solution may be obtained. This information includes particle size, shape, mass, and distributions of these quantities. Light scattering can also give information about interactions taking place between species of particles, such as hetero- and self-association and aggregation. FIG. 1 illustrates how a conventional light scattering measurement is made within a single well of a multiwell plate. In this depiction a beam of light 1 is emitted by a light scattering source, often a laser 2 and is transmitted through the well 3 of a multiwell plate partially filled with a sample containing fluid 4. A detector 5 gathers scattered light from the measurement volume 6, which consists of the region of intersection between the laser beam and the area subtended by the field of view of the detector 5. In the case of a SLS measurement, the detector is generally a photodiode. For DLS measurements the detector may be a photon counting module such as an avalanche photodiode (APD) or a photomultiplier tube (PMT). As discussed previously, light scattered or reflected from any object or surface may reach the detector or cause significant background scattering and lead to erroneous results. It is very important, therefore, to have a high degree of certainty that scattered light received by the detector 5 is indeed from the sample, and not from errant scattering sources.

Figure 2:
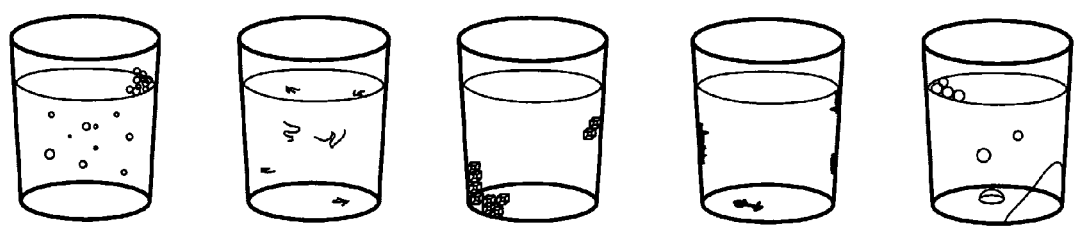
FIG. 2 illustrates various possible contaminants which may be contained within or on the surface of sample vessels.

Examples of wells with possible elements of contamination are shown in FIG. 2. As discussed previously, bubbles on the surface of the sample, adhering to the walls or floor of the vessel, or floating within in the sample may cause unwanted background scattering. Bubbles may also form or dissolve as the temperature of the sample is varied, and knowledge of the evolution of these bubbles is helpful to determine the reliability of any light scattering measurements of the sample. Similarly dust particles, precipitated particles, crystals, imperfections in the surfaces of the wells, and oil residue, among other contaminants, may deleteriously affect light scattering measurements.

One means to provide greater assurance that light scattering measurements are, in fact, collected from the desired scattering source is to optically observe the condition of the measurement cell in which the sample is contained. This may be accomplished, perhaps most simply by visual inspection. However, visual inspection is not always possible nor practical, for example, when light scattering data is being acquired from a sample as a function of temperature or within the confines of light scattering instrument. Consider a light scattering measurement in a 1536 well plate being ramped through 50° C. with the objective of taking one measurement from each cell per 1° C. of the temperature ramp. This experiment would result in tens of thousands of measurements where conditions may have prompted the formation of a bubble in one or more of the samples contained in the multiwell plate. It is simply not practical to visually observe each well at each measurement temperature, particularly when the well plate is located within a sealed, temperature regulated instrument. Visual inspection is also unlikely to be the most accurate method available. Using an optical camera, by contrast, may enable a non-subjective means by which the suitability of the wells for light scattering measurements may be ascertained. Image analysis for object determination and/or intensity variation over a range of imaged wells offers an objective means to quantify the likelihood of a well being physically contaminated. However, the operation of a camera in the tight confines of a light scattering instrument may be exceedingly difficult, and it is made significantly more so by the difficulties associated with providing proper illumination to the sample in order for the camera to record images of any usefulness.

Modern light scattering instruments generally utilize high powered diode laser systems which can greatly improve the signal-to-noise ratio of the measurements. However, the very nature of the laser used introduces problems with direct illumination of the sample container by a secondary light source. If, for example, the laser source is introduced into the sample from beneath an optically transparent plate, a diffuse, uniform light source, such as would be useful in illumination for a camera, would likely be in the way of the laser beam as it exits the sample and thus would very likely be damaged thereby. It is therefore necessary to provide a means by which a diffuse illumination may be provided to the sample and/or vessel that does not interfere with the operation of the laser source used for the light scattering measurement. Further if illumination of the container for imaging by a camera is provided from the bottom of the multiwell plate, strong reflections of the source from the bottom surface of the multiwell plate itself may overwhelm any image data of the well and its contents.

Figure 3:
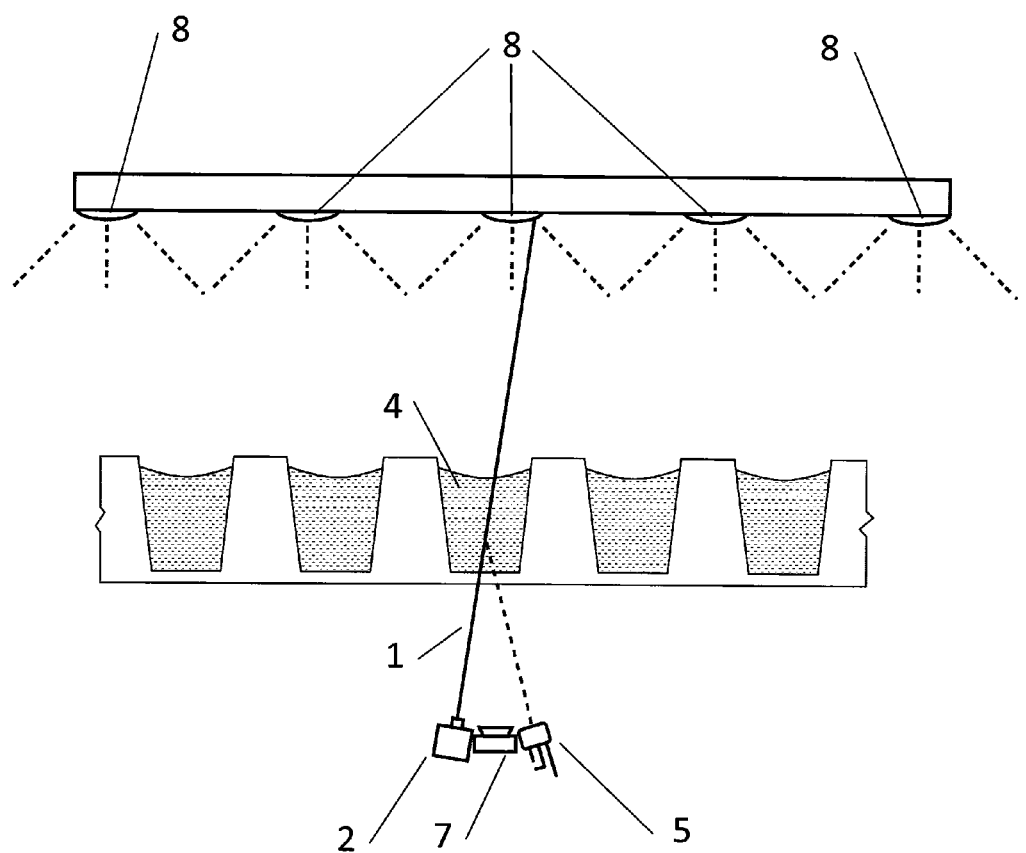
FIG. 3 shows a multiwell sample vessel wherein imaging illumination is provided from above by diffuse light sources, and light scattering illumination of the sample well and detection of scattered light from said sample are from below.

Lighting the sample from above is not trivial. As illustrated in FIG. 3, in a possible configuration of acquisition of DLS data, illumination is provided by diffuse light sources 8, and images of the sample and vessel are recorded by camera element 7. A tightly focused laser beam 2 is shining up through the sample 4, and having that laser beam impact a light source 8 above the well might both damage the light source 8 and result in a spray of background laser light which would negatively impact the DLS measurements. It is therefore preferred to employ a different means to apply diffuse light to the sample and containing vessel to enable imaging by the camera 7.

Figure 4:
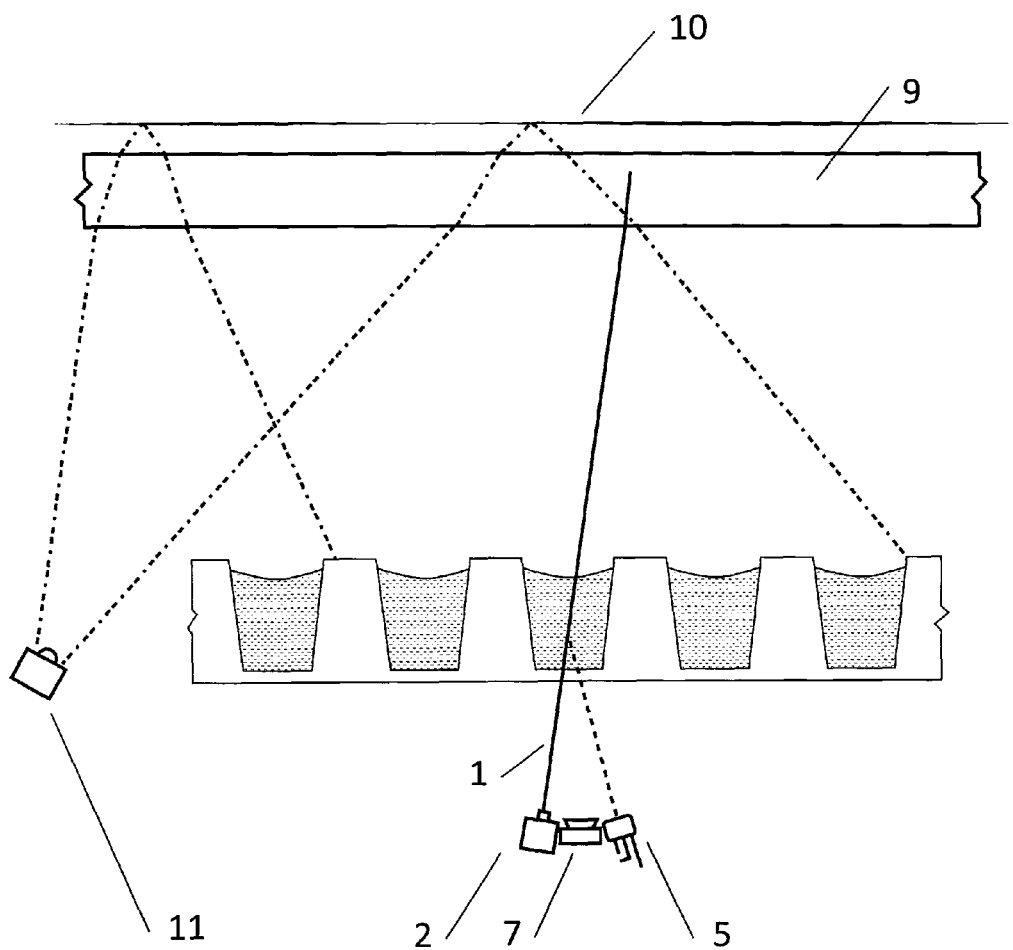
FIG. 4 shows an embodiment of the present invention where the light from an imaging illumination source is directed to an absorbing/transmitting optical structure placed above a multiwell sample container or vessel. Light from this source is transmitted through the absorbing/transmitting optical structure and reflects and/or scatters off a diffuser, providing illumination to the sample from above. A light scattering source produces a beam of a different wavelength that is directed through the sample contained within the multiwell sample vessel, and upon exiting therefrom the light scattering source beam is absorbed by the absorbing/transmitting optical structure.

In order to overcome the lighting challenges described above, the innovative design of the present invention makes use of an absorbing/transmitting optical structure located above the sample and well as shown in FIG. 4. This absorbing/transmitting optical structure 9, absorbs light at the wavelength of the light scattering source used, but transmits light at other wavelengths. A preferred embodiment of the present invention, shown in FIG. 4, utilizes as a first light source 2, such as a laser, employed for the light scattering measurements. This source creates the light scattering beam 1 at a wavelength of $\lambda_1$. The light scattering source beam passes through the sample, in this case contained within a well of a multiwell plate, by traversing the bottom of a multiwell measurement vessel and then through the sample. The light scattering beam emerges from the sample contained within the multiwell plate, and impinges upon the absorbing/transmitting optical structure 9 located above the multiwell vessel. This optical structure has been selected to absorb radiation at the wavelength of the light scattering source, $\lambda_1$. A second source, the image illumination source 11, emits illumination at a different wavelength, $\lambda_2$, or range of wavelengths, and its beam is incident at an angle on the absorbing/transmitting optical structure 9, generally made of a special glass plate, which is located above the sample wells. This absorbing/transmitting optical structure absorbs light at the wavelength of the laser, $\lambda_1$, but transmits at least some of the light emitted by the image illumination source 11. Optical filter glass, which absorbs at particular wavelengths and which may be employed as the absorbing/transmitting optical structure, is available from optical suppliers such as Schott North America, Inc. (Elmsford, N.Y.). The transmitted light from the imaging illumination source is then scattered and reflected from a diffusing surface 10, such as a plain sheet of white paper, and after transmission back through the absorbing/transmitting optical structure 9 illuminates the wells from above. The absorbing/transmitting optical structure therefore acts as a "beam dump" for the light scattering source, while transmitting light required for illumination at a wavelength which the camera is able to register.

The absorbance and transmittance of the optical structure may be chosen to correspond to the wavelengths of the two light sources, or vice versa, and some variation of wavelengths $\lambda_1$ and $\lambda_2$ may be possible. For example, an absorbing/transmitting optical structure may be chosen which absorbs at 830 nm±30 nm, but transmits at all other wavelengths. Therefore the wavelength of the laser may operate anywhere within that range or on the peripheries thereof so long as the beam is adequately absorbed by the plate such that light scattering signals are not deleteriously affected and the instrument is not damaged. Therefore, the values of $\lambda_1$ and $\lambda_2$ may vary by, possibly up to 10% based on the absorbance specifications of the absorbing/transmitting optical structure used. Alternatively, this optical structure may be selected which absorbs and transmits in a range that appropriately matches the wavelengths of light chosen. Further the wavelength of $\lambda_2$ may not be particularly relevant, and may encompass a wide variety of wavelengths or combinations thereof, for example white light, so long as the camera 7 is able to detect a sufficient intensity of light that an image may be created or other useable data gathered therefrom.

While a plain sheet of white paper may act as a diffusing surface 10, it is also possible to use any number of other surfaces, such as a diffusing plastic produced by 3M (St. Paul, Minn.), so long as they aid in the diffusion of light to be transmitted back through the absorbing plate 9. A thin weatherproof vinyl sheet has also proven very useful as a diffusing element 10. One particular advantage of this specific element is that the weatherproofing of the sheet aids in maintaining the integrity of the diffusing sheet over many temperature ramping cycles, which may be common in high throughput light scattering experiments, among other applications. Further the diffusing surface need not even be an additional element, but rather could be a special diffusing surface incorporated into the glass or a special diffusing layer or coating adhered or placed thereon.

Additionally, the absorbing/transmitting optical structure could reflect light from an imaging illumination source which produces diffuse light, such as a tungsten bulb, fluorescent tube or properly diffused light emitting diode. In this case a coating applied to a surface on which the illumination source beam impinges would reflect light at a wavelength or wavelengths different from that of the light scattering source, but transmit light into the absorbing/transmitting optical structure at the wavelength of the light scattering source. For example, a glass plate to which has been applied a coating which transmits light at 830 nm, but reflects light at 530 nm could serve as the absorbing/transmitting optical structure. In this example, the light scattering source operates near 830 nm, and the beam is transmitted through the coating into the glass plate. The imaging illumination source may emit light at 530 nm, and the light reflected from the coating serves as the illumination source for the camera.

Additionally, other coatings may be applied to a surface of the absorbing/transmitting optical structure in order to enhance the absorption and/or transmission at specific wavelengths. For example, a broad band anti-reflection coating can improve transmission at particular wavelengths, such as those which might be employed by the imaging illumination source.

Figure 5:
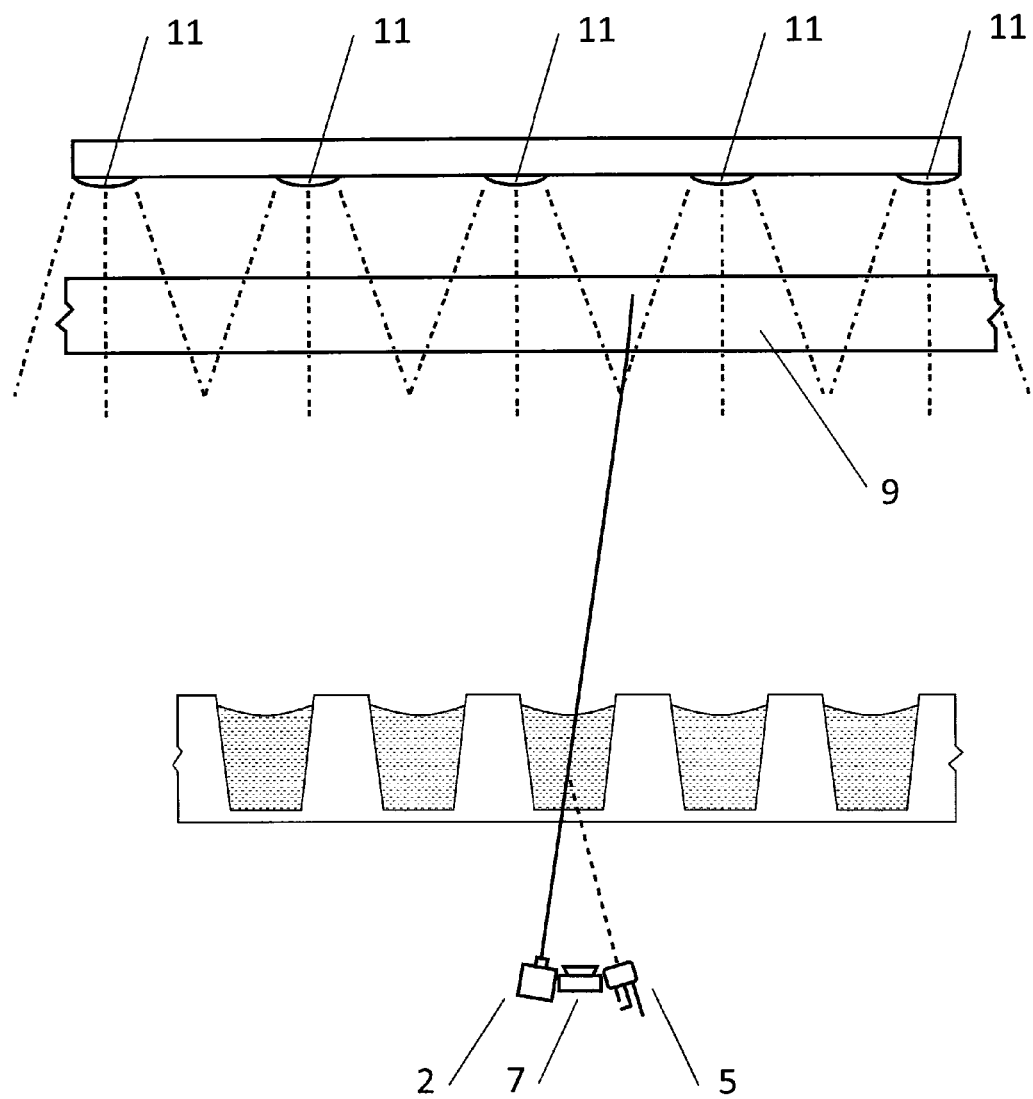
FIG. 5 shows another embodiment of the invention similar to that illustrated in FIG. 4, but with imaging illumination sources emitting diffuse light from above the absorbing/transmitting optical structure.

Another embodiment of the present invention is illustrated in FIG. 5. In this implementation, rather than having the imaging illumination source located below or to the side of the multiwell plate, one or more imaging illumination sources may be located above the absorbing/transmitting optical structure. In contrast to the problematic arrangement of elements shown in FIG. 3, the absorbing/transmitting optical structure 9 acts as a beam dump as described above and prevents the light scattering source beam from causing damage to the imaging illumination source or sources as well as preventing the beam from scattering or reflecting off of other surfaces in the instrument which may lead to erroneous measurements of light gathered by detector 5.

While the preferred embodiments of the present invention generally place both the light scattering source 2 and the detector 5 beneath the multiwell plate, as shown in FIGS. 4 and 5, it is not necessary that the detector 5 be located on the same side of the multiwell plate as the light scattering source so long as the absorbing/transmitting optical structure 9 and the light scattering source are located on the opposite sides of the multiwell plate. Further, the imaging illumination source or sources may be located beneath the multiwell plate, so long as the multiwell plate permits transmission of light from the imaging illumination source there through of a wavelength that will not be absorbed by the absorbing/transmitting optical structure. In such a configuration care must be taken to avoid reflections which may overwhelm the light received by the camera. It should further be noted that the invention should not be limited to embodiments wherein the light scattering detector and camera are analyzing the same sample at the same time. Indeed, when an instrument is acquiring light scattering data, it may be most efficient for the camera to be located such that it is acquiring an image of the a located adjacent to the well be analyzed by light scattering.

It should further be noted that there is no limitation on the maximum number of light sources which may be employed. Multiple imaging illumination sources 11 may aid in improving the imaging ability of the camera 7, and/or may provide better uniformity across a multiwell plate. It is also possible that multiple light scattering sources and detectors may be used in a single instrument. Further a multiplicity of cameras may be operated simultaneously to provide images and/or data which might be beyond the field of view of a single camera. Further, multiple cameras may be operated to image the same area, but at different focal planes. Therefore it should be clear that any number of imaging illumination sources, light scattering sources, detectors, and cameras, and any combination of these elements may be employed and not depart from the spirit of the invention.

Image data acquired and generated by the camera 7 may be used in many ways to determine the status of each sample well. Each image may be individually viewed by an operator to visually inspect contents of the well. For example, small bubbles may be visible in an image which corresponds to a given sample well, and the operator of the instrument may choose to disregard any data coming therefrom. If an image accompanies data taken from a sample, analysis of the data may take into consideration visual inspection of the image for possible contaminants. However, other methods of analysis may be employed to determine the likelihood of accurate light scattering data having been collected from a given sample well. For example a multiwell plate may be scanned using a method and apparatus discussed above, and an average taken of the intensity values of all wells containing sample. Any wells which have an average intensity above a selected threshold as measured by the camera may be targeted for further inspection of the images to determine whether data collected therefrom should be included in the analysis. This method can be particularly useful when large numbers of samples are collected from 384 and 1536 multiwell plates. Other similar analyses, such as object detection algorithms and other techniques known in the art, may be employed as well to determine the likelihood of a sample well being contaminated. For example object detection algorithms may be used to analyze the images captured from the camera to identify the presence of a bubble or bubbles within a well.

While the discussion above has concerned itself primarily with dynamic light scattering measurements in multiwell plates, the disclosed invention should not be considered limited to either of these constraints. Any light scattering measurements may benefit from this novel imaging apparatus and system, including SLS and/or DLS measurements in multiwell plates, cuvettes or flow cells, phase analysis light scattering (PALS) measurements performed in flow through cells, cuvettes, or other specialized measurement cells, or existing as single droplets, among others. PALS and massively parallel PALS (MP-PALS) are discussed in detail in pending U.S. patent application Ser. No. 12/782,682, by Hsieh and Trainoff filed Mar. 18, 2010, which is hereby incorporated by reference. Additionally, the fluorescence of a sample may be measured by the optical camera or the light scattering measurement detector if the sample fluoresces when illuminated by either the light scattering source or the image illumination source. The present invention is particularly useful for cases where geometry limits light scattering and image acquisition illumination to be largely along the same axis, however, constraints of engineering may make it beneficial to place these illumination sources on the same axis if, for example, space within an instrument is highly limited, or more analysis techniques are used, such as measuring UV absorbance and dynamic light scattering within the same volume simultaneously or near simultaneously.

There are many embodiments of our invention that will be obvious to those skilled in the arts of measurement optics that are but simple variations of our basic invention herein disclosed that do not depart from the fundamental elements that we have listed for their practice; all such variations are but obvious implementations of the invention described hereinbefore and are included by reference to our claims, which follow.

The invention claimed is:

1. A method for recording an image of a liquid-borne sample previously prepared for light scattering measurement, said light scattering measurement made by transmitting a light beam of wavelength $\lambda_1$ through said liquid-borne sample, where said light beam, after traversing said sample, intersects an absorbing/transmitting optical structure selected to absorb light selectively in a wavelength range spanning $\lambda_1$, and some fraction of light scattered by said sample is allowed to fall upon a detector, where said image is recorded by the method comprising the steps of A) providing illumination from one or more imaging illumination sources operating at a wavelength different from $\lambda_1$ or at range of wavelengths, said range of wavelengths not including $\lambda_1$, said imaging illumination passing through said absorbing/transmitting optical structure, said absorbing/transmitting optical structure is selected to permit the transmission of at least a portion of said imaging illumination, thereby illuminating said liquid-borne sample; and B) recording an image produced of said liquid-borne sample.

2. The method of claim 1 where said image is recorded by optical camera means.

3. The method of claim 2 wherein said optical camera means comprises multiple cameras.

4. The method of claim 2 comprising the further step of displaying said recorded image on a computer monitor.

5. The method of claim 2 comprising the further step of storing a digital representation of said recorded image in a computer memory means.

6. The method of claim 5 comprising the further step of correlating said stored image with data corresponding to said light scattering measurement from the same liquid sample.

7. The method of claim 1 comprising the further step wherein said imaging illumination having traversed said absorbing/transmitting optical structure, is incident upon a diffusion means which reflects and/or scatters light, a portion of said reflected and/or scattered light is transmitted back through said absorbing/transmitting optical structure, thereby illuminating said liquid-borne sample.

8. The method of claim 7 where said diffusion means is a weatherproofed vinyl sheet.

9. The method of claim 1 comprising the further step of analyzing said recorded image to determine a relative likelihood of said measured scattered light being an accurate representation of the light scattered from sample alone.

10. The method of claim 1 where said liquid sample is held within a container.

11. The method of claim 10 where said container is a well of a microwell plate.

12. The method of claim 10 where said container is a cuvette.

13. The method of claim 1 wherein said light scattering measurement is a static light scattering measurement.

14. The method of claim 1 wherein said light scattering measurement is a dynamic light scattering measurement.

15. The method of claim 1 wherein said light scattering measurement is a phase analysis light scattering measurement.

16. The method of claim 1 comprising the further step of measuring fluorescence of said sample due to said imaging light source.

17. An apparatus for measuring light scattered from a liquid-borne sample and recording an image of said sample comprising
  A) light scattering illumination source which transmits a beam of light of wavelength $\lambda_1$ through said sample;
  B) a detector oriented to detect light from said light scattering illumination source which is scattered by said sample;
  C) an absorbing/transmitting optical structure positioned such that it intersects the path of said beam from said light scattering illumination source after traversing said sample,
  D) imaging illumination means which generates light at a wavelength different from $\lambda_1$ or at a range of wavelengths, said range of wavelengths not including $\lambda_1$, positioned such that at least a portion of the light generated therefrom is transmitted through said absorbing/transmitting optical structure; and
  E) imaging means positioned to record an image of said sample,
where said absorbing/transmitting optical structure is selected so as to both absorb light selectively in a wavelength range spanning $\lambda_1$, and to permit the transmission of at least a portion of said light generated by said imaging illumination means.

18. The apparatus of claim 17 further comprising a diffusion means positioned such that a fraction of the light from said imaging illumination means, after passing through said absorbing/transmitting optical structure is reflected and/or scattered therefrom and a portion of said reflected and/or scattered illumination is transmitted back through said absorbing/transmitting optical structure, thereby illuminating said liquid-borne sample.

19. The apparatus of claim 18 wherein said diffusion means is a weatherproofed vinyl sheet.

20. The apparatus of claim 17 wherein said absorbing/transmitting optical structure is a glass plate which absorbs light at or near the wavelength of said light scattering source, $\lambda_1$.

21. The apparatus of claim 20 wherein one surface of said glass plate is at least partially coated with an anti-reflection layer.

22. The apparatus of claim 17 wherein said light scattering illumination source is a laser.

23. The apparatus of claim 22 wherein $\lambda_1$ is 830 nm.

24. The apparatus of claim 17 wherein said absorbing/transmitting optical structure allows transmission of light at 530 nm.

25. The apparatus of claim 17 wherein said imaging illumination means comprises one or more light emitting diodes.

26. The apparatus of claim 17 wherein said imaging illumination means comprises a plurality of imaging illumination sources.

27. The apparatus of claim 26 wherein said plurality of imaging illumination sources produce diffuse light.

28. The apparatus of claim 17 wherein said imaging means comprises one or more optical cameras.

29. The apparatus of claim 17 further comprising a Peltier heater/cooler unit in contact with said absorbing/transmitting optical structure, said Peltier heater/cooler is capable of dissipating heat within said absorbing/transmitting optical structure generated by absorption of said light scattering illumination source beam.

30. The apparatus of claim 17 wherein said imaging illumination means is located on the same side of said absorbing/transmitting optical structure as said light scattering illumination source.

31. The apparatus of claim 17 wherein said absorbing/transmitting optical structure is located between said imaging illumination source and said sample.

32. The apparatus of claim 17 wherein said absorbing/transmitting optical structure is coated such that light from said imaging illumination source transmitted there through is reflected by said coating.

* * * * *